(12) United States Patent
Koyanagi

(10) Patent No.: US 8,834,022 B2
(45) Date of Patent: Sep. 16, 2014

(54) RADIATION CASSETTE CARRIER AND PORTABLE RADIATION IMAGING APPARATUS

(75) Inventor: Takahiro Koyanagi, Kawasaki (JP)

(73) Assignee: Canon Kabushiki Kaisha, Tokyo (JP)

( * ) Notice: Subject to any disclaimer, the term of this patent is extended or adjusted under 35 U.S.C. 154(b) by 287 days.

(21) Appl. No.: 13/277,345

(22) Filed: Oct. 20, 2011

(65) Prior Publication Data

US 2012/0134477 A1 May 31, 2012

(30) Foreign Application Priority Data

Nov. 29, 2010 (JP) ................................. 2010-265431

(51) Int. Cl.
H01L 27/146 (2006.01)
A61B 6/00 (2006.01)

(52) U.S. Cl.
CPC ................ A61B 6/4283 (2013.01); A61B 6/56 (2013.01)
USPC ...... 378/189; 378/98.8; 378/204; 250/370.09

(58) Field of Classification Search
USPC ............ 378/19, 91, 98.8, 189, 190, 192, 204, 378/210; 250/370.01, 370.08, 370.09, 526
See application file for complete search history.

(56) References Cited

U.S. PATENT DOCUMENTS

| | | | | |
|---|---|---|---|---|
| 3,419,670 A | * | 12/1968 | Schneider | 174/135 |
| 3,813,634 A | * | 5/1974 | Wigby et al. | 439/459 |
| 3,858,160 A | * | 12/1974 | Denton | 174/135 |
| 5,064,967 A | * | 11/1991 | Singbartl | 174/549 |
| 5,533,911 A | * | 7/1996 | Elam | 439/459 |
| 6,904,149 B2 | * | 6/2005 | Keenum et al. | 379/445 |
| 7,482,595 B1 | * | 1/2009 | Ertel | 250/370.09 |
| 7,540,660 B2 | | 6/2009 | Koyanagi | 378/189 |
| 2010/0044575 A1 | * | 2/2010 | Kito | 250/370.09 |
| 2010/0158197 A1 | * | 6/2010 | Jadrich et al. | 378/189 |
| 2010/0202589 A1 | * | 8/2010 | Ohta et al. | 378/98 |

FOREIGN PATENT DOCUMENTS

JP 10-282598 10/1998
JP 3577003 7/2004

* cited by examiner

*Primary Examiner* — Anastasia Midkiff
(74) *Attorney, Agent, or Firm* — Fitzpatrick, Cella, Harper & Scinto

(57) ABSTRACT

A cassette carrier for containing a cassette incorporating a semiconductor radiation detector includes a rectangular recessed portion formed for containing the cassette with an irradiation surface exposed. The recessed portion is formed by a first frame that forms a side wall of one side thereof and includes a handle that a user holds, and a second frame forming a side wall of another side of the recessed portion. In the side wall formed by the first frame, an opening is provided in an opposite position opposing a connector unit of the cassette with the cassette attached to the recessed portion. The first frame has a space in communication with the opening, and connection/disconnection of an external cable to/from the connector unit is possible through the space with the cassette attached, and the space is large enough to contain an entire connector housing of the external.

12 Claims, 5 Drawing Sheets

RADIATION CASSETTE CARRIER AND PORTABLE RADIATION IMAGING APPARATUS

BACKGROUND OF THE INVENTION

1. Field of the Invention

The present invention relates to a radiation cassette carrier for providing portability to a radiation cassette and portable radiation imaging apparatus using the radiation cassette carrier.

2. Description of the Related Art

Generally, apparatuses that obtain an X-ray image by irradiating a target object with X-rays and detecting the intensity distribution of X-rays that have been transmitted through the target object are widely used in the field of industrial nondestructive testing and medical diagnosis. General methods of imaging include the film/screen system and the CR (Computed Radiography) system. In these systems, a photosensitive film or a phosphor plate that stores an image as a latent image is placed in a housing case called a cassette, which is standardized by JIS Z 4905, and used in image-taking. When taking an image, an operation for aligning the target object and the cassette in a desired position is necessary, but the cassette has a rectangular parallelepiped shape, and no particular consideration is given to how a user will hold the cassette. Therefore, as disclosed in Japanese Patent Laid-Open No. 10-282598 (hereinafter referred to as "Patent Document 1"), a cassette carrier has been proposed that stores a cassette in a central portion thereof and has handle portions on both sides.

Meanwhile, a DR (Digital Radiography) system has been also proposed in which an X-ray image is captured and digitalized using a semiconductor sensor, and the size and weight of apparatuses have been reduced with improvements in packaging technology, resulting in commercialization of portable X-ray imaging apparatuses. However, since such apparatuses incorporate a large number of electronic components, they are heavier than conventional cassettes. Accordingly, as disclosed in Japanese Patent No. 3577003 (hereinafter referred to as "Patent Document 2"), an apparatus in which a handle portion for holding is formed in the casing of an x-ray detection portion has been developed.

When taking an x-ray image in a medical setting, various platforms such as a platform for use in the upright position or a table for use in the lying position are used for positioning and holding the cassette with respect to a subject. Many of these platforms that are installed are designed in conformity with the external shape of the cassette standardized by JIS Z 4905. If the shape or size of an X-ray detection portion utilizing the DR system is different from the size of the standardized cassette, a new platform will be needed to match the DR X-ray detection portion, which increases the investment costs. Therefore, provision of an X-ray imaging apparatus compatible with the external shape of the cassette specified by JIS Z 4905 has been desired. Due to advancement in high-density packaging technology and wireless technology, X-ray imaging apparatuses having a shape compatible with the standardized cassette have been developed. However, on the other hand, the portability taken into account with conventional DR apparatuses is compromised, and a cassette carrier such as disclosed in Patent Document 1 becomes necessary.

With a configuration for housing a cassette as disclosed in Patent Document 1, wireless communication performance is degraded, and thus measures that take account of wireless communication performance are necessary. Also, it may no longer be possible to access to a wired connection portion or an operation portion provided in the cassette. It is conceivable to provide a relay cable or a connector in the cassette carrier, and enable wired connection to the stored cassette. However, when connection is established through a relay cable of the cassette carrier, EMC (electromagnetic compatibility) may deteriorate or the external size of the cassette carrier may increase. Furthermore, in Patent Document 2, a handle is formed in the casing, and thus although it is easy to achieve a design that can bear the strength load applied when positioning the imaging portion with respect to the subject, the design will deviate from external shape of the standardized cassette.

SUMMARY OF THE INVENTION

The present invention has been achieved in view of the above-described problems, and according to an embodiment of the present invention, a radiation cassette carrier is provided that achieves portability with a semiconductor radiation detection panel attached thereto, while maintaining the wireless communication performance, wired communication performance and operability thereof.

According to one aspect of the present invention, there is provided a radiation cassette carrier for containing a cassette that incorporates a semiconductor radiation detector, the radiation cassette carrier comprising: a rectangular recessed portion that is formed for containing the cassette in a state in which an irradiation surface is exposed; a first frame that forms a side wall of one side of the recessed portion and includes a handle; and a second frame that forms a side wall of another side of the recessed portion, wherein in the side wall formed by the first frame, an opening is provided in an opposite position opposing a connector unit of the cassette in a state in which the cassette is attached to the recessed portion, the first frame has a space in communication with the opening, and connection/disconnection of an external cable to/from the connector unit is possible through the space in a state in which the cassette is attached, and the space is large enough to contain an entire connector housing of the external cable, in a case where the external cable is connected to the connector unit in a state in which the cassette is attached to the recessed portion.

Also, according to another aspect of the present invention, there is provided a portable radiation imaging apparatus comprising: the above-described radiation cassette carrier; and a radiation cassette incorporating a semiconductor radiation detector.

Further features of the present invention will become apparent from the following description of exemplary embodiments with reference to the attached drawings.

DESCRIPTION OF THE EMBODIMENTS

Hereinafter, exemplary embodiments of the present invention will be described with reference to the attached drawings.

First Embodiment

A portable radiation imaging apparatus configured by a radiation cassette that incorporates a semiconductor radiation detector and a radiation cassette carrier that contains the radiation cassette and also provides portability will be described below. Note that in the following embodiment, a configuration using X-rays as radiation, that is, a portable X-ray imaging apparatus configured by an X-ray cassette and a cassette carrier that contains the X-ray cassette will be described as an example.

Figure 1:
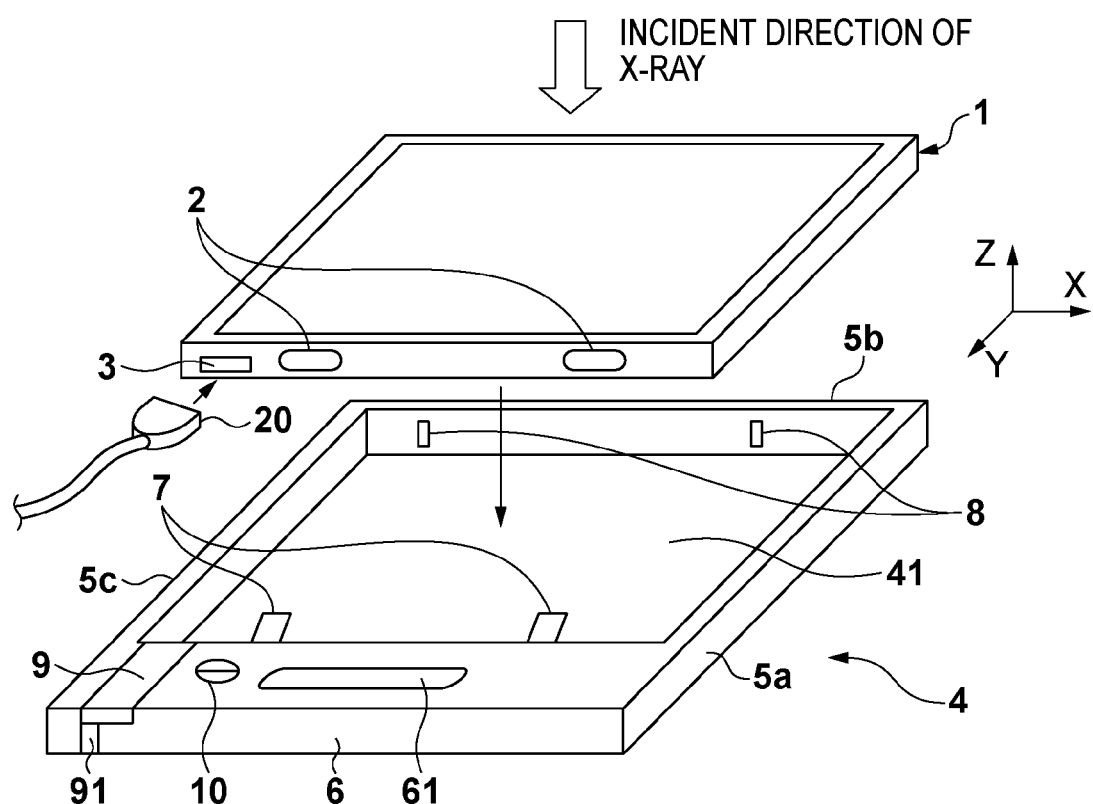
FIG. 1 is a diagram illustrating a basic configuration of a portable X-ray imaging apparatus according to a first embodiment.
Figure 2:
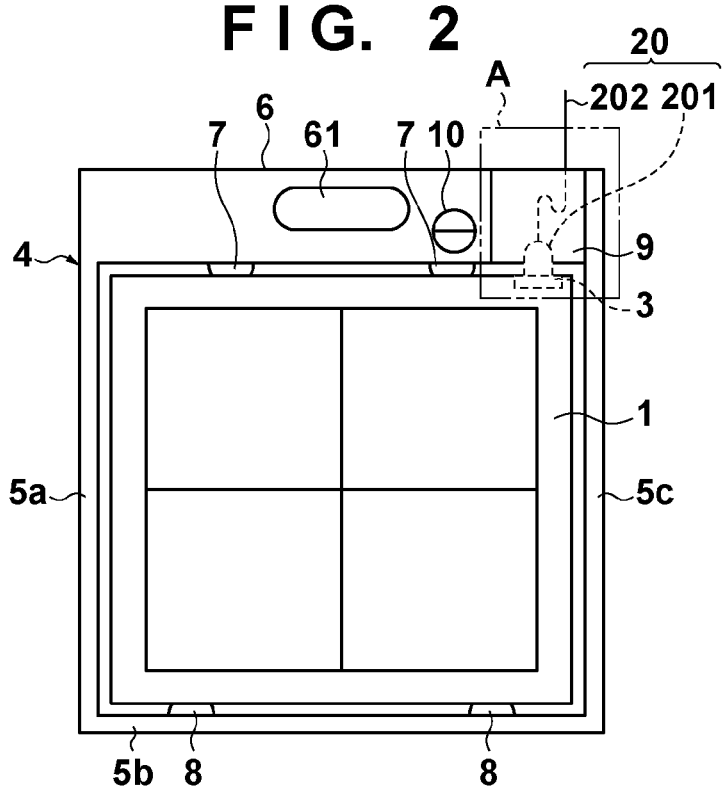
FIG. 2 is a front view of the portable X-ray imaging apparatus according to the first embodiment.

The configuration of a portable X-ray imaging apparatus according to the present embodiment is shown in FIGS. 1 and 2. The portable X-ray imaging apparatus according to the present embodiment includes two units, namely, an X-ray cassette 1 and a cassette carrier 4. The X-ray cassette 1 is a cassette whose external shape and size comply with those of the cassette standardized by JIS Z 4905, and incorporates a semiconductor X-ray detector (not shown in the drawings), a wireless communication circuit, a wired communication circuit, a battery and the like. With the configuration of the X-ray cassette 1 as described above, a device for fitting the cassette standardized by JIS Z 4905 thereinto can be used without alteration. Also, on a side face of the casing of the X-ray cassette 1, a connector unit 3 to which an external cable is connected is provided. This configuration enables power supply to the X-ray cassette 1, and sending and receiving of signals to and from the X-ray cassette 1 by connecting an external cable 20 that is connected to an external control unit or an external power supply unit, not shown in the drawings, to the connector unit 3.

On the other hand, the cassette carrier 4 is provided as a unit to and from which the X-ray cassette 1 can be attached and detached, in order to improve portability when the X-ray cassette 1 is used in a free position, in a medical trolley, for example. The cassette carrier 4 has a rectangular recessed portion 41 in which the X-ray cassette 1 is contained with the irradiation surface thereof exposed. The recessed portion 41 is formed by a bottom face panel and side walls of the four sides surrounding the bottom face panel. A first frame 6 provides a side wall of one of the four sides of the recessed portion 41, and second frames 5a to 5c provide side walls of the remaining three sides. Note that a through hole is formed in the first frame 6 which provides a handle 61 that the operator can hold.

In the side wall of the recessed portion 41 formed by the second frame 5b, protrusions 8 are formed. Groove portions, not shown in the drawings, are provided in a side face of the X-ray cassette 1 in positions corresponding to the protrusions 8. By inserting the protrusions 8 into these groove portions, the X-ray cassette 1 is prevented from coming out of the recessed portion 41 in the Z direction when the X-ray cassette 1 is contained in the recessed portion 41. In addition, in the side wall opposing the side wall where the protrusions 8 are provided (the side wall formed by the first frame 6), locking protrusions 7 are provided. The locking protrusions 7 have a mechanism with which the locking protrusions 7 can move in the Y direction. The mechanism for moving the locking protrusions 7 in the Y direction is arranged inside the first frame 6, and is linked to a locking operation portion 10. Accordingly, as a result of the user operating the locking operation portion 10, the locking protrusions 7 can be moved in the Y direction. The user first inserts the protrusions 8 into the groove portions (not shown in the drawings) of the X-ray cassette 1, angles the X-ray cassette 1 into the recessed portion 41 so as to be contained therein, and operates the locking operation portion 10 to insert the locking protrusions 7 into groove portions 2 of the X-ray cassette 1, thereby achieving a locked state.

In addition, in a state where the X-ray cassette 1 is housed in the recessed portion 41 of the cassette carrier 4, the connector unit 3 for wired communication is arranged opposing the side wall formed by the first frame 6. In the side wall formed by the first frame 6, an opening is provided in a portion that opposes the connector unit 3 in a state in which the X-ray cassette 1 is attached to the recessed portion 41. The first frame 6 has a space (reference numeral 600 in FIG. 3) in communication with the opening, and connection/disconnection of the external cable 20 to/from the connector unit 3 is thus made possible in a state in which the X-ray cassette 1 is attached to the recessed portion 41. Note that FIG. 1 illustrates a state in which the space 600 is closed by a connector cover 9. The space 600 will be described in detail below with reference to FIG. 3.

With the cassette carrier 4 having a configuration as described above, in a state in which the X-ray cassette 1 is attached to the recessed portion 41, the X-ray cassette 1 is surrounded by the bottom face panel of the recessed portion 41, the second frames 5a to 5c and the first frame 6, thereby improving mechanical strength. This is effective for protecting the X-ray cassette 1, which is expensive, since the cassette carrier 4 may be dropped or hit when it is carried. In particular, when an image is taken during a patient visit, for example, an X-ray detection portion may be moved in and out from underneath the subject lying on his or her side on the bed. Even in the case where the load is applied in the Z direction, the cassette carrier 4 has a structure that can sufficiently bear the load with the bottom face panel of the recessed portion 41.

Furthermore, the lock mechanism for the locking protrusions 7 and the space 600 for accessing the connector unit 3 for wired connection of the X-ray cassette 1 are arranged on the side of the first frame 6 of the cassette carrier 4. Therefore, on the remaining three side faces, the distance to the contour of the imaging region of the X-ray cassette 1 can be minimized. As a result, the three side faces can be disposed as close as possible to a desired site when imaging is performed.

Also, the first frame 6 is configured such that the cable cover 9 can open and close the space 600 (FIG. 3) for accessing the connector unit 3. Therefore, it is possible to connect the external cable 20 to the connector unit 3 in a state in which the X-ray cassette 1 is fitted into the cassette carrier 4. Note that the cable cover 9 may be attached to the first frame 6 by hinges or the like so as to be openable and closable, or may be detachable from the first frame 6.

In a state in which the space 600 is closed by the cable cover 9, a lead portion 91 for leading the external cable 20 to the outside is formed. The space 600 has a size with which the entirety of a connector housing 201 of the external cable 20 can be contained in the case where the external cable 20 is connected to the connector unit 3 with the X-ray cassette 1 attached to the recessed portion 41. Thus, by adopting a configuration in which the cable cover 9 can be attached with the external cable 20 being connected to the connector unit 3, it is possible to protect the connector unit 3 of the X-ray cassette 1 or the connector housing 201 of the external cable 20 such that load in the Z direction is not applied thereto during image-taking, for example. That is, a configuration is adopted that can reduce the risk of damage of the connector unit 3 and the connector housing 201.

Figure 3:
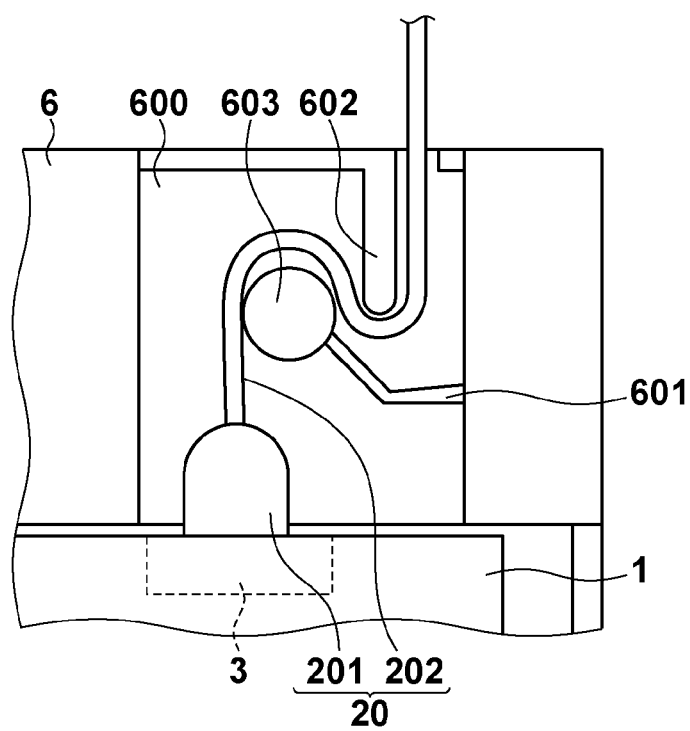
FIG. 3 is a detailed diagram of a portion A of the portable X-ray imaging apparatus according to the first embodiment.

FIG. 3 is a detailed diagram of a state in which the cable cover 9 is removed near an external cable connection portion (portion A in FIG. 2) in the first embodiment. In the first frame 6, the space 600 for cable wiring is formed. By providing a wall 601 in the space 600, a cable 202 is restricted so as not to be misrouted, and the cable 202 is laid in an S shape by wiring guides 602 and 603. By securing such a laying route of the cable, a configuration is adopted in which when the external cable 20 is connected to the connector unit 3 of the X-ray cassette 1, load is not applied to the connector housing 201 with respect to a pulling force of the cable (force in the Y direction).

With the configuration of the first embodiment as described above, the following operations are made possible.
  taking an image after fitting the X-ray cassette 1 into a device for fitting the cassette standardized by JIS Z 4905 thereinto
  improving portability and mechanical strength by attaching the X-ray cassette 1 to the cassette carrier 4, and taking an image from a medical trolley or the like Also, image-taking with a medical trolley is performed at various places, and thus it is assumed that image-taking will be performed by wired connection in places where wireless communication is prohibited or stable wireless communication cannot be achieved. Also, with the configuration of the present embodiment described above, cable connection can be used without impairing portability or operability.

Note that in the above-described embodiment, a configuration is shown in which the four sides of the recessed portion 41 are surrounded by the second frames 5a to 5c and the first frame 6, the configuration is not limited to this. Although strength is slightly reduced, by adopting a configuration in which the recessed portion 41 is formed by the side wall of the first frame 6 and at least one of the side walls of the second frames 5a to 5c, the X-ray cassette 1 can be attached to the cassette carrier 4, and thus it is possible to provide portability. For example, the recessed portion 41 may be formed by only the second frame 5b and the first frame 6 (the side wall provided by the first frame 6 and the opposite side wall). Alternatively, for example, the recessed portion 41 may be formed by the second frames 5a and 5b and the first frame 6 (the side wall provided by the first frame 6 and two side walls including the opposite side wall).

Second Embodiment

In the first embodiment, load applied to the connector unit 3 and the connector housing 201 by operating or carrying the X-ray cassette 1 is reduced by providing the cable cover 9. However, when the X-ray cassette 1 to which the external cable 20 is connected is to be removed from the cassette carrier 4 with the cable cover 9 attached thereto, the connector housing 201 and the cable cover 9 interfere with each other. As a result, the connector housing 201 or the cable cover 9 may be damaged.

Figure 4:
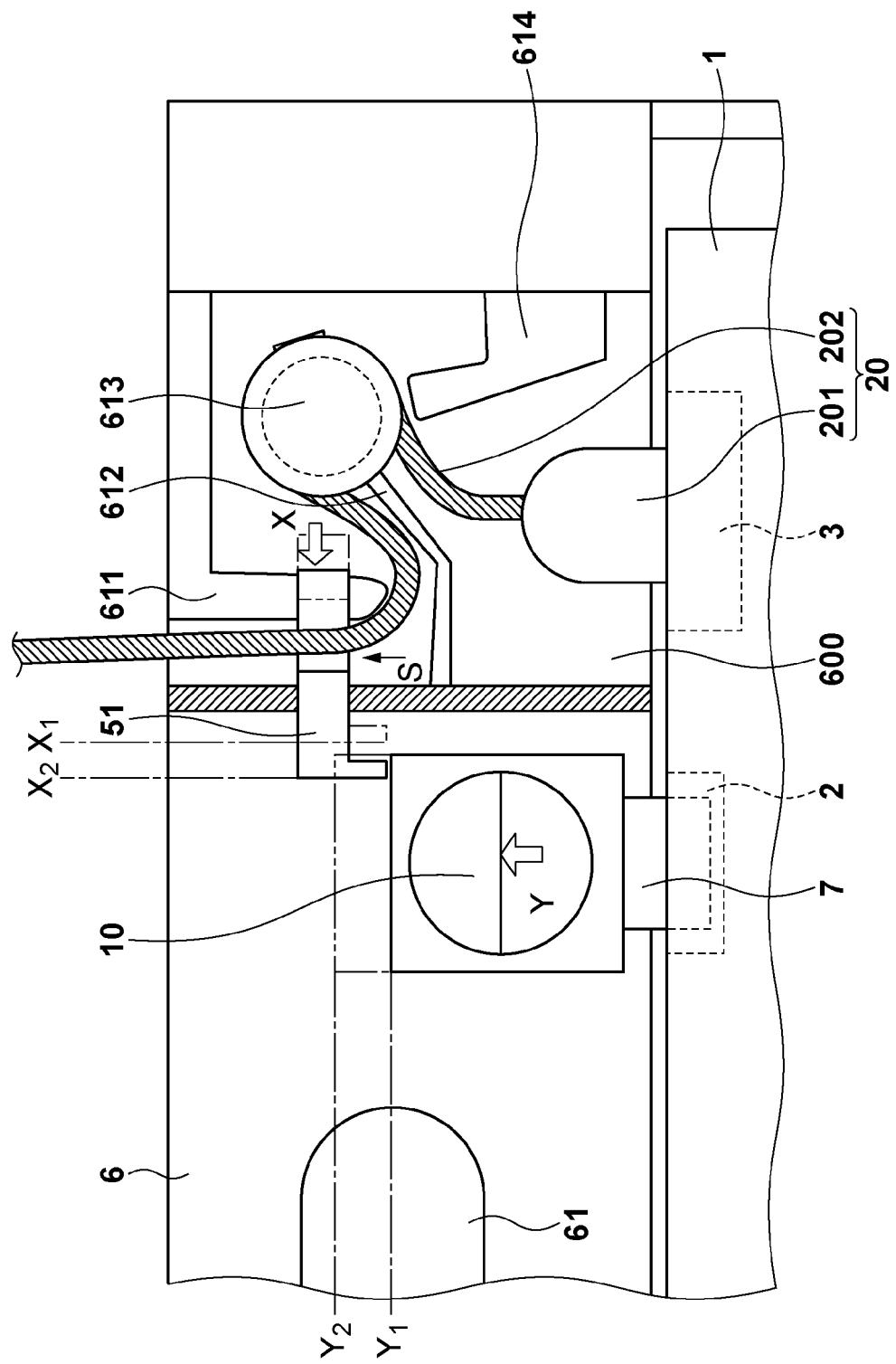
FIG. 4 is a lateral cross-sectional view of a portable X-ray imaging apparatus according to a second embodiment.

In view of this, a mechanism realized by taking reduction of damage due to a wrong operation procedure into account will be described with reference to FIGS. 4 and 5. FIG. 4 is a diagram illustrating the configuration of a space 600 and a lock mechanism of a second embodiment. Note that the elements that are the same as those described in the first embodiment are assigned the same reference numerals.

In the cassette carrier 4 of the present embodiment, in the case where the external cable 20 is connected to the connector unit 3, the locked state of a lock mechanism for keeping the X-ray cassette 1 attached to the recessed portion 41 is inhibited from being released due to physical interference with the external cable 20. This configuration will be described below in further detail.

Figure 5A:
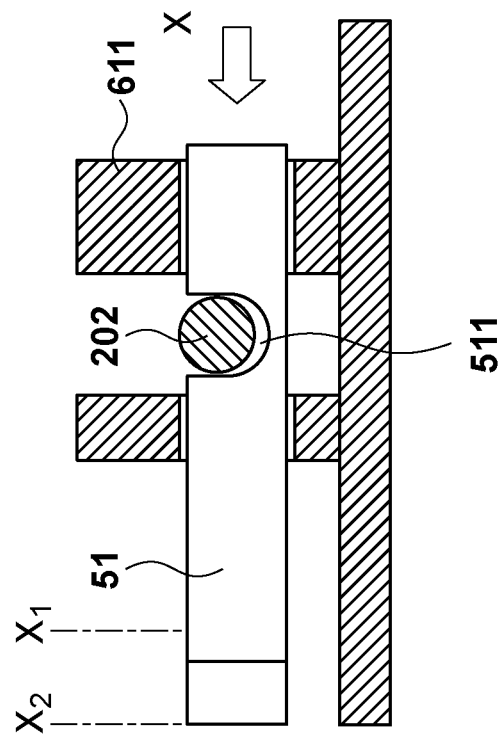
FIGS. 5A and 5B are front views of the portable X-ray imaging apparatus according to the second embodiment.
Figure 5B:
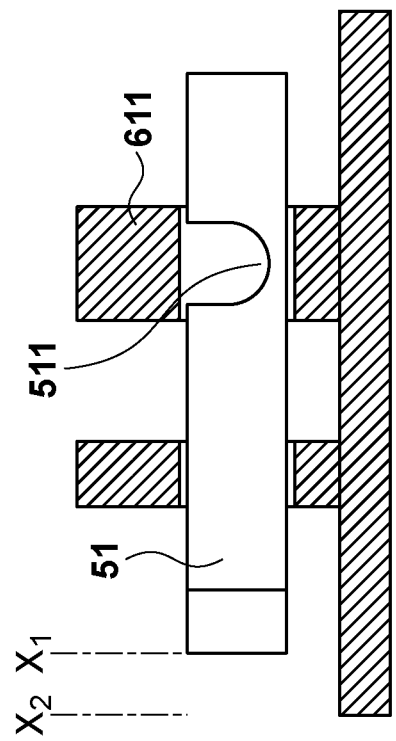

A structure for laying the external cable 20 is formed in the space 600 of the cassette carrier 4. By providing a wall 612, the cable 202 is restricted so as not to be misrouted, and the external cable 20 is laid in an S shape with wiring guides 611, 613 and 614. By securing such a laying route of the cable 202, a configuration is adopted in which when the external cable 20 is connected, load due to a pulling force of the cable (force in the Y direction) is not applied to the connector housing 201 or connector unit 3 of the X-ray cassette 1. To the wiring guide 611 near the lead portion 91 of the cable 202, a restriction lever 51 is attached so as to be capable of sliding in the X direction. FIGS. 5A and 5B each show the position of the restriction lever 51 as viewed from the direction S, in the case where the external cable is present and the case where the external cable is not present. In the restriction lever 51, a U-shaped groove 511 through which the cable 202 can be laid is formed.

In FIG. 5A, the restriction lever 51 is positioned at $X_1$ due to a spring (not shown in the drawings). In FIG. 5B, the U-shaped groove 511 is positioned in the laying route as a result of the restriction lever 51 being pushed in the direction of the arrow X so as to be moved to a position $X_2$. By fitting the cable 202 in the U-shaped groove 511, the restriction lever 51 is fixed at the position $X_2$.

By pushing the locking operation portion 10 shown in FIG. 4 in the direction of the arrow Y so as to be moved from a lock position $Y_1$ to a lock position $Y_2$, the locked state of the locking protrusions 7 is released. However, when the external cable 20 is laid as described above, the restriction lever 51 is positioned at $X_2$ and thus the locking operation portion 10 cannot be moved to the release position $Y_2$. Therefore, the locked state established by the locking protrusions 7 cannot be released, and the X-ray cassette 1 cannot be removed from the recessed portion 41. That is, while the external cable 20 is connected, the X-ray cassette 1 cannot be removed from the recessed portion 41, and thereby damage of the connector unit 3, the connector housing 201, or the connector cover 9 can be prevented.

Figure 6:
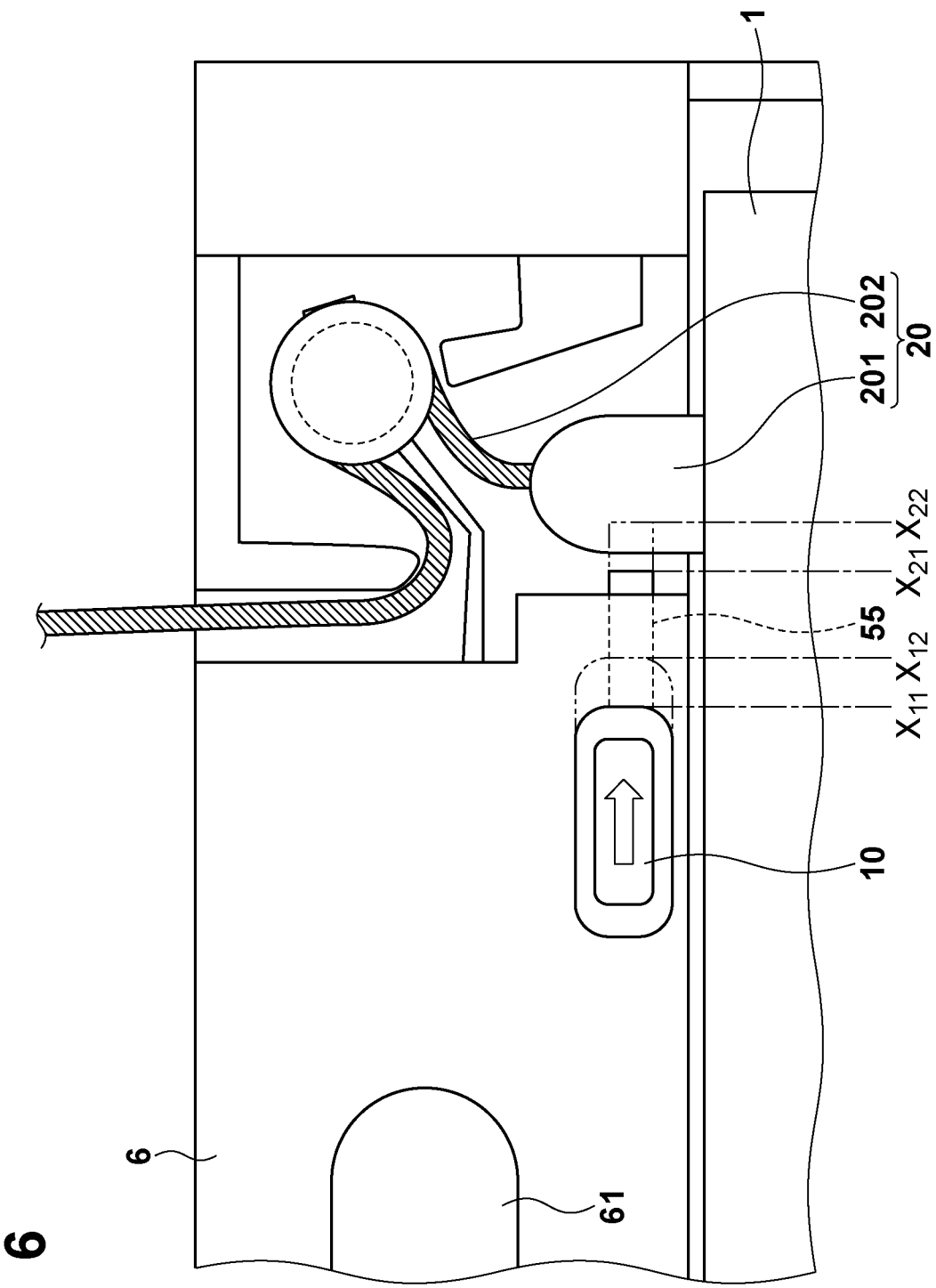
FIG. 6 is a back view of the portable X-ray imaging apparatus according to the second embodiment.

Note that a configuration where releasing of the lock mechanism is inhibited due to physical interference with the external cable 20 (connector housing 201 and cable 202) is not limited to the above-described configuration, and needless to say, various variations are possible. For example, as shown in FIG. 6, the cassette carrier 4 is assumed to have a lock mechanism in which the tip of a lock release lever 55 is moved from a position $X_{21}$ to a position $X_{22}$ when the locking operation portion 10 is slid from a position $X_{11}$ to a position $X_{12}$, and thereby the locked state with respect to the X-ray cassette 1 is released. In FIG. 6, while the external cable 20 is connected, the tip of the lock release lever 55 linked to the locking operation portion 10 is subjected to physical interference by the connector housing 201 of the external cable 20, thereby making releasing of locked state impossible.

As described above, according to the second embodiment, since a mechanism inhibiting incorrect operation that prevents release of the lock when the external cable 20 is connected is included, the second embodiment has an effect of preventing damage to the connector unit 3 and the connector housing 201.

As described above, according to the foregoing embodiments, it is possible to achieve the followings in a portable radiation imaging apparatus in which a radiation cassette having an external shape compatible with that of a film cassette is attached to the cassette carrier:
  sufficient strength for bearing load applied during carriage or use
  usability and sufficient protection against load applied to the cable when the cable is connected The radiation cassette carrier of the present invention can provide portability with a cassette incorporating a semiconductor radiation detection panel attached thereto, while maintaining wireless communication performance, wired communication performance and operability thereof.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2010-265431 filed Nov. 29, 2010, which is hereby incorporated by reference herein in its entirety.

What is claimed is:

1. A radiation cassette carrier constructed to contain a cassette that incorporates a radiation detector, the radiation cassette carrier comprising:
   a containing portion for containing the cassette; and
   a lock mechanism for keeping the cassette in a state in which the cassette is attached to said containing portion,
   wherein, in said lock mechanism, releasing of a locked state is inhibited due to physical interference with a cable, in a case where the cable is connected to the cassette from outside of said containing portion.

2. The cassette carrier according to claim 1, further comprising
   a guide for, in a state in which the cassette is attached to said containing portion, guiding and holding a cable from the cassette such that the cable is laid in an S shape.

3. The cassette carrier according to claim 2, wherein said guide is provided in a space which communicates with a first opening provided on an inner side wall of said containing portion and a second opening provided on an outer side wall of said containing portion, and
   said cassette carrier further comprises a connector cover for opening and closing said space.

4. The cassette carrier according to claim 3, wherein said first opening and said second opening are arranged in positions that are mutually displaced in a direction of the connection/disconnection of a connector to/from the cassette.

5. The cassette carrier according to claim 4, wherein said guide guides a cable from said first opening to said second opening such that the cable is laid in an S shape in said space.

6. A portable radiation imaging apparatus comprising:
   a radiation cassette carrier according to claim 1; and
   a radiation cassette incorporating a radiation detector.

7. The cassette carrier according to claim 2, wherein said guide is provided in a space which communicates with a first opening provided on an inner side wall of said containing portion and a second opening provided on an outer side wall of said containing portion, and
   wherein said guide further comprises:
       a first wiring guide which restricts the cable laid through said first opening in a direction away from said inner side wall; and
       a second wiring guide which restricts the cable laid through said first wiring guide in a direction away from said outer side wall.

8. The cassette carrier according to claim 7, wherein said first wiring guide has a side wall and has a guiding groove for guiding the cable on said side wall, and has an arcuate shape.

9. The cassette carrier according to claim 7, wherein said first wiring guide comprises a wall which is connected to a side wall between said first opening and said second opening.

10. The cassette carrier according to claim 1, wherein said containing portion comprises:
    a rectangular recessed portion that is formed for containing the cassette in a state in which an irradiation surface is exposed;
    a first frame that forms a side wall of one side of said recessed portion and includes a handle; and
    a second frame that forms a side wall of another side of said recessed portion,
    wherein, in said side wall formed by said first frame, an opening is provided in an opposite position opposing a connector unit of the cassette in a state in which the cassette is attached to said recessed portion,
    said first frame has a space in communication with said opening, and connection/disconnection of an external cable to/from said connector unit is possible through said space in a state in which the cassette is attached, and
    said space is large enough to contain an entire connector housing of the external cable, in a case where the external cable is connected to said connector unit in a state in which the cassette is attached to said recessed portion.

11. The cassette carrier according to claim 2,
    wherein said lock mechanism comprises a restriction lever attached to at least a portion of the guide so as to be capable of sliding a groove for laying the cable in a direction across the cable, and a locking operation portion for releasing the cassette from the state in which the cassette is attached to said containing portion, and
    wherein said locking operation portion is configured not to be able to release the cassette from the state in which the cassette is attached to said containing portion when the cable is laid on the groove.

12. A radiation cassette carrier for containing a cassette that incorporates a semiconductor radiation detector, the radiation cassette carrier comprising:
    a rectangular recessed portion that is formed for containing the cassette in a state in which an irradiation surface is exposed;
    a first frame that forms a side wall of one side of said recessed portion and includes a handle; and
    a second frame that forms a side wall of another side of said recessed portion,
    wherein, in said side wall formed by said first frame, an opening is provided in an opposite position opposing a connector unit of the cassette in a state in which the cassette is attached to said recessed portion,
    said first frame has a space in communication with the opening, and connection/disconnection of an external cable to/from the connector unit is possible through the space in a state in which the cassette is attached,
    said space is large enough to contain an entire connector housing of the external cable, in a case where the external cable is connected to the connector unit in a state in which the cassette is attached to said recessed portion,
    said first frame further comprises a lock mechanism for keeping the cassette in a state in which the cassette is attached to said recessed portion, and
    in said lock mechanism, releasing of a locked state is inhibited due to physical interference with the external cable, in a case where the external cable is connected to the connector unit.

* * * * *